United States Patent [19]

Singh

[11] Patent Number: 5,516,662

[45] Date of Patent: May 14, 1996

[54] PROCESS FOR THE PREPARATION OF HEADGROUP-MODIFIED PHOSPHOLIPIDS USING PHOSPHATIDYLHYDROXYALKANOLS AS INTERMEDIATES

[75] Inventor: Alok Singh, Springfield, Va.

[73] Assignee: The United States of America as represented by the Secretary of the Navy, Washington, D.C.

[21] Appl. No.: 439,074

[22] Filed: May 11, 1995

Related U.S. Application Data

[62] Division of Ser. No. 99,639, Jul. 30, 1993, Pat. No. 5,441,876.

[51] Int. Cl.$^6$ .................................................. C12P 9/00
[52] U.S. Cl. ............................................................ 435/131
[58] Field of Search ............................ 435/131; 554/78, 554/79

[56] References Cited

U.S. PATENT DOCUMENTS

| | | | |
|---|---|---|---|
| 4,235,792 | 11/1980 | Hsia et al. | 260/403 |
| 4,382,035 | 5/1983 | Eibl | 260/403 |
| 4,587,055 | 5/1986 | Regen | 260/413 |
| 4,624,919 | 11/1986 | Kokusho et al. | 435/74 |
| 4,783,402 | 11/1988 | Kokusho et al. | 435/52 |
| 4,849,019 | 7/1989 | Yasukawa et al. | 106/244 |
| 4,933,114 | 6/1990 | O'Brien et al. | 260/403 |
| 5,011,964 | 4/1991 | Mynarcik et al. | 558/179 |
| 5,080,911 | 1/1992 | Saitou et al. | 426/32 |
| 5,183,750 | 2/1993 | Nishide et al. | 435/134 |
| 5,188,951 | 2/1993 | Tremblay et al. | 435/131 |

FOREIGN PATENT DOCUMENTS

| | | |
|---|---|---|
| 200403 | 4/1986 | European Pat. Off. . |
| 62-205788 | 9/1987 | Japan . |
| 831129 | 5/1981 | U.S.S.R. . |
| 1581810 | 12/1980 | United Kingdom . |
| WO89/01524 | 2/1989 | WIPO . |

OTHER PUBLICATIONS

Mank et al., "Synthesis of acyl di–and triglycerols", *Chemistry and Physics of Lipids*, vol. 50, 1989, pp. 63–70.

Singh et al., "Phosphatidylhydroxyalkanols As Versatile Intermediates In The Synthesis Of Headgroup Modified Diacetylenic Phospholipids", *Synthetic Communications*, vol. 22, No. 16, Sep. 1992, pp. 2293–2304.

Achterberg et al., "Conversion Of Radiolabelled Ethanolamine Plasmalogan Into The Dimethylethanolamine And Choline Analogue Via Transphosphatidylation By Phospholipase D From Cabbage", *Chemistry and Physics of Lipids*, vol. 41, 1986, pp. 349–353.

Yang et al., "Transphosphatidylation by Phospholipase D", *J. Biol. Chem.*, vol. 242, No. 3, 1966, pp. 477–484.

Chrastil et al., "Phospholipases C and D in Rice Grains", *J. Agric. Food Chem.*, vol. 35, No. 4, 1987, pp. 624–627.

Shuto et al., "A Facile One–Step Synthesis Of Phosphatidylhomoserines By Phospholipase D–Catalyzed Transphosphatidylation", *Chem. Pharm. Bull.*, vol. 25, No. 1, 1987, pp. 447–449.

Ali et al., "Mixed–chain phosphatidylocholine analogues modified in the choline moiety: preparation of isomerically pure phospholipids with bulky head groups and one acyl chain twice as long as the other", *Chemistry and Physics of Lipids*, vol. 50, 1989, pp. 11–21.

Juneja et al., "Repeated batch and continuous operations for phosphatidylglycerol synthesis from phosphatidylcholine with immobilized phospholipase D", *Appl. Microbiol. Biotechnol.*, vol. 27, 1987, pp. 146–151.

Juneja et al., "Comparative study on conversion of phosphatidylchlorine to phosphatidylcylcerol by cabbage phospholipase D in micelle and emulsion systems", *Enzyme and Microbiol. Technol.*, vol. 9, No. 6, 1987, pp. 350–354.

Markowitz, MA et al., *Cheml Phys. Lipids* 62:193–204 (1992).

Manyemana, F. et al. *Tetrahedron Lett.* 30:3077–80 (1989).

Nan, Z. et al., *Huaxue Shiji* 14:117–18 (1992).

Primary Examiner—Michael G. Wityshyn
Assistant Examiner—S. Saucier
Attorney, Agent, or Firm—Thomas E. McDonnell; Barry A. Edelberg

[57] ABSTRACT

Phospholipase D enzyme is used to mediate the synthesis of a phosphatidylhydroxyalkanol in a first step. This phosphatidylhydroxyalkanol is reacted to produce a headgroup modified phospholipid in a subsequent step. In the first step, phospholipase D enzyme extract mediates transphosphatidylation of a phospholipid with an alcohol containing at least two hydroxyl groups per molecule, producing reproducible and nearly quantitative yields of a phosphatidylhydroxyalkanol. In the subsequent step, the hydroxyl head group of the phosphatidylhydroxyalkanol is further reacted with amino, carboxylic, halogen or thiol containing molecules to produce a headgroup modified phospholipid.

2 Claims, No Drawings

PROCESS FOR THE PREPARATION OF HEADGROUP-MODIFIED PHOSPHOLIPIDS USING PHOSPHATIDYLHYDROXYALKANOLS AS INTERMEDIATES

This is a division of application Ser. No. 08/099,639, filed Jul. 30, 1993, now U.S. Pat. No. 5,441,876, to Alok Singh, titled PROCESS FOR THE PREPARATION OF HEADGROUP-MODIFIED PHOSPHOLIPIDS USING PHOSPHATIDYLHYDROXYALKANOLS AS INTERMEDIATES.

BACKGROUND OF THE INVENTION

1. Field of the Invention

The present invention relates to a process for the preparation of phospholipids having modified headgroups and, more particularly, to a process of using phosphatidylhydroxyalkanols as intermediates in the preparation of headgroup modified phospholipids.

2. Description of the Related Art

Phospholipids, such as phosphocholines (polymerizable and synthetic), are used to form technologically attractive, stable lipid membranes, the utility of which is well established in fields such as encapsulation and controlled release, ion-transport, molecular recognition and biosensors. Synthetic alternations in the phospholipid molecules have not only made it possible to fabricate molecularly engineered supramolecular assemblies but also to stabilize the resultant microstructures through polymerization. Phospholipids have been modified, both in the polar headgroup region and in the acyl chain region to meet the specific goal desired for the membrane, including stabilization schemes, site for protein immobilization, controlled release strategies, molecular recognition and sensor development. To extend the applicability of lipid membranes, the charge neutral headgroup of phosphocholines need to be replaced with reactive functionalities which provide sites for further surface modification. The most straightforward routes reported for the synthesis of such headgroup modified lipids have been the phospholipase D mediated transphosphatidylation of phosphocholines with substituted alkanols. Such straightforward routes are not synthetically attractive due to the low yields of products, and the dependence of transphosphatidylation on the reaction conditions, chain length of alkanols as well as the nature of the acyl chains.

For example, in the synthesis of headgroup modified diacetylenic phospholipids by transphosphatidylation, the nature and origin of phospholipase D enzyme plays an important role. Phospholipase D enzyme derived from cabbage exchanges short chain alkanols, but not long chain alkanols, with choline moiety of natural and synthetic phospholipids. Phospholipase D enzyme isolated from rice germ facilitates exchanges of alkanols independent of their chain length. Phospholipase D enzyme extracted from streptomyces catalyzes the transfer of higher alcohols with natural phosphocholines, but remains ineffective on synthetic phosphocholines, mixed chain cholines and bulky choline groups. Similarly, pure phospholipase D enzyme from cabbage or peanut does not produce reproducible yields of diacetylenic phosphatidylethanolamine or phosphatidylbromoethanol.

Alternate synthetic routes involve multi-step, time consuming, low yield chemical synthesis. Furthermore, the reaction conditions involved in these alternate synthetic routes are often incompatible with the polymerizable moieties in lipids which are useful in developing further technological applications.

Thus, there is a need for a convenient, reproducible and high yield general synthetic route for the preparation of a variety of headgroup modified phospholipids.

SUMMARY OF THE INVENTION

The present invention overcomes these problems by using phospholipase D enzyme mediated synthesis to produce a phosphatidylhydroxyalkanol in a first step and chemical reactions the phosphatidylhydroxyalkanol to produce a headgroup modified phospholipid in a subsequent step. In the first step, phospholipase D enzyme extract is used to mediate transphosphatidylation of a phospholipid with an alcohol containing at least two hydroxyl groups per molecule, producing reproducible and nearly quantitative yields of a phosphatidylhydroxyalkanol. In the subsequent step, the hydroxyl headgroup of the phosphatidylhydroxyalkanol is further reacted with amino, carboxylic, halogen or thiol containing molecules to produce a headgroup modified phospholipid. The present invention provide a convenient and effective process for the preparation of headgroup modified phospholipids.

DETAILED DESCRIPTION OF THE PREFERRED EMBODIMENT

The present invention is a two step process for the synthesis of a headgroup modified phospholipid, comprising:

transphosphatidylating, in the presence of phospholipase D enzyme, a phospholipid with an alcohol containing at least two hydroxyl groups per molecule to form a phosphatidylhydroxyalkanol; and reacting the phosphatidylhydroxyalkanol with an amino, halogen, carboxylic or thiol containing molecule to form the headgroup modified phospholipid.

In the first step, the phospholipase D enzyme may be, for example, isolated from rice germ, extracted from streptomyces, cabbage or peanut. Preferably, the phospholipase D enzyme is extracted from white leaves of cabbage. The phospholipid is preferably phospholipid 1,2-bis-(tricosa-10, 12-diynoyl)-sn-glycero-3-phosphocholine ($DC_{8,9}PC$), although the invention may also be applied to modify the headgroups of other phospholipids. In order to provide a hydroxyl group for further reaction in the second step, the alcohol must be at least a diol. The alcohol may be, for example, a water-soluble diol having primary —OH groups, such as diethylene glycol, ethylene glycol, 1,3 propanediol, 1,4-butanediol, glycerol, and the like.

In the second step, the phosphatidylhydroxyalkanol is used as a reactive intermediate to produce, for example, esters and halo (Cl, Br or I) analogues of the phosphatidylhydroxyalkanol. Typically, the halogenating agent is an N,N, 2-trialkyl-1-halopropenylamine. Preferably, the halogenating agent is an N,N, 2-trimethyl-1-halopropenylamine, an N,N, 2-triethyl-1-halopropenylamine or an N,N, 2-tributyl-1-halopropenylamine. The halogenating reagent converts the phosphatidylhydroxyalkanol into halogenated analogues in high yields. These halogenated analogues may be further reacted with alkylamines to give aminophospholipids in good yield. These alkylamines used are preferably primary or secondary, and may be water-soluble or insoluble. Typical alkylamines useful in the present invention include methylamine, dimethylamine, iminodiacetic acid, and the like. The phosphatidylhydroxyalkanol may also be reacted with maleic anhydride, for example, to produce an ester linked carboxyl terminated lipid.

Moreover, the present invention is also applicable to the synthesis of polymerizable phospholipids containing metal chelating iminodiacetic acid functionality in their headgroup region. In this case, the hydroxy group of the phosphatidylhydroxyalkanol is reacted with, for example a sulfuryl halide, such as sulfuryl chloride, to produce a reactive halide intermediate in quantitative yield. This intermediate, upon reaction with an amine, for example, a primary alcoholic amine such as N,N (bis carboxymethyl) ethanolamine, provides a phospholipid with a headgroup having a metal chelating iminodiacetic acid functionality. Furthermore, the method can be extended to increase the linker length between sulfur and nitrogen without going through complex reaction sequence. The ability to control the length and nature of the linkers is advantageous in the study of membrane interactions with biomolecules and ions. For example, the hydroxy group of the phosphatidylhydroxyalkanol may be reacted with a dimethyl dihalosilane, $-SiX_2(CH_3)_2$ (where X is Cl, I or Br) to form a reactive intermediate and control the length of the linker. Either of these reactive intermediates (from sulfuryl halide or dimethylhalosilane) may also be reacted, for example, with any primary alcohol, R—OH (water-soluble or water-insoluble), including saccharides. In the reaction of the reactive halide intermediate with a primary alcohol, an ether linkage, —OR replaces the halogen, —X, of the phospholipid, to form useful phospholipids having etherified headgroups.

The present invention has broad applicability in modifying phospholipids because of a) long shelf-life of phospholipase D from. cabbage extract (one month at −20° C.), b) almost quantitative enzymatic transformations and c) mild reaction conditions.

Materials and Methods

Phospholipase D was extracted from white leaves of cabbage following the procedure reported by Eibl and Kovatchev in *Methods Enzym.*, vol. 72, p. 632, 1981, which is incorporated herein by reference. The protein content in the extract was measured to be 1.7 mg/ml. The enzyme extract was stored in a freezer and used as such. The extract remained active for one month.

Polymerizable phospholipids, such as 1,2-bis (tricosa-10,12-diynoyl)-sn-glycero-3-phosphocholine ($DC_{8,9}PC$), have the following formula:

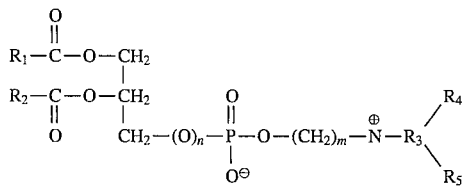

wherein, as in all the following formulae, $R_1$ and $R_2$ may each be an alkyl group containing at least one polymerizable group, such as a an acrylic acid ester group, an acrylate group, a diacetylenic group or a diene functionality and may be the same or different, n is 0 to 1, m is 2, 3 or 4 and $R_3$, $R_4$ and $R_5$ may each represents an alkyl group containing 1 to 4 carbon atoms and may be the same or different. For example, the compound wherein $R_1$ and $R_2$ are both $-(CH_2)_8-C{\equiv}C-C{\equiv}C-(CH_2)_9-CH_3$, and $R_{3-5}$ are all $-CH_3$ was synthesized following the procedures reported by Leaver et al., *Biochem. Biophys. Acta*, vol. 732, p. 210, 1983; Singh, *J. Lipid Res.*, vol. 31, p. 1522, 1990; and Gupta et al., *Proc. Natl. Acad. Sci. USA*, vol. 74, p. 4315, 1977, which are incorporated herein by reference.

Ether was dried over calcium chloride. Acetate buffer (pH 5.6) containing 0.2M sodium acetate and 0.08M calcium chloride was used in the enzyme catalyzed reactions. Ethylene glycol, propane diol, butanediol, ethylene diaminetetraacetic acid (EDTA) were obtained from Aldrich Chemical Company. For efficient transformations, the enzyme extract:buffer ratio was kept at 1.75:1, the volume of ether was kept three times that of the acetate buffer, and the phospholipid concentration was maintained at 0.66% of the total volume in the reaction flask.

The course of the phospholipase reaction was monitored by thin layer chromatography on silica gel (Merck) employing two solvent systems; chloroform:methanol:water (65:25:4) (A), and chloroform:methanol:ammonia (25% in water) (65:30:3) (B). Spray reagent phosphomolybdic acid was made in the lab according to established procedure and Dragendorff's reaction was purchased from Sigma Chemical Company. N,N,2-trimethyl-1-chloropropenylamine was synthesized following the procedures reported by Munyemana et al., *Tetrahedron Lett.*, vol.30, p. 3077, 1989 and Haveaux et al., *Org. Synth.*, vol. 59, p. 26, 1980, which are incorporated herein by reference, in their entireties and for all purposes. Infrared spectra were obtained using a Perkin-Elmer 1800 FT-IR. NMR spectra were obtained in $CDCl_3$ using a Varian EM 390 or Brucker MSL 360 nuclear magnetic resonance spectrometer. Mass spectral analysis was carried out by fast atom bombardment (FAB) mass spectrometry using a Finnigan triple quadrupole mass spectrometer to insure both the molecular identity and the absence of calcium ions in the sample.

The phospholipase reaction is performed at temperatures and pH's suitable for the action of the enzyme. Typically, temperatures of about 20°–40° C., and pH of about 4 to about 7.5 may be used. Preferably, the temperature is about 25°–30° C. and the pH is about 5.6–6.5.

The concentration of enzyme in the system may affect the speed of the phospholipase reaction. Generally, the higher the concentration of enzyme, the faster the reaction. The General Procedure outlined below uses close to the minimum practical concentration of enzyme that one might wish to use.

Calcium is essential to the phospholipase reaction used in the present invention. The concentration of calcium in the reaction system should therefor be at least about 14 mM While the phospholipase reaction occurs using phospholipase D derived from any biological source, the phospholipase reaction of the present invention will not occur if the pure enzyme, rather than a crude preparation (i.e., direct extract, without affinity separation) is used. Apparently, the presence of a substance associated with phospholipase D, and found in the biological sources of that enzyme, stabilizes its active form.

General Procedure for the Synthesis of Phosphatidylhydroxyalkanol 500 mg (0.55 mmols) of 1,2-bis(tricosa- 10,12-diynoyl)-sn-glycero-3-phosphocholine ($DC_{8,9}PC$) was dissolved in 30 mL of ether with gentle warming. A one hundred-fold excess of an appropriate diol, as discussed below, was added. At 40° C. a translucent solution was obtained. Then, a mixture of the phospholipase D extract (30 mL) and 0.2M aq. acetate (NaOAc—AcOH) buffer (80 mM $CaCl_2$, pH 5.6)

(17 mL) was added. A pinkish color developed. An additional 20 mL ether was added. The reaction mixture was stirred vigorously at 40° C. The course of the reaction was monitored by thin layer chromatography (TLC) on silica plates using solvent systems A and B. Phosphatidylhydroxyalkanols were revealed at $R_f$ 0.53 as compared with $R_f$ 0.33 for phosphocholine (PC) in solvent A, and in solvent B phosphatidylhydroxyalkanols were revealed at $R_f$ 0.69 as compared with $R_f$ 0.17 for PC. The reaction mixture was stirred for 10 hours. During this time, the reaction mixture was protected from light. The ether was evaporated under reduced pressure and 100 mL of a saturated aq. EDTA solution (pH 8.5) was added to the remaining aqueous phase. The lipid was extracted thrice with a 2/1 $CHCl_3/CH_3OH$ (v/v) mixture. The organic fractions were combined and the solvent was evaporated under reduced pressure at 45° C. The residue was redissolved in a minimum amount of $CHCl_3$ and the purity of the lipid was analyzed by thin layer chromatography (solvent A). The developed plates were analyzed using Dragendorff's reagent to monitor the disappearance of the PC. The appearance of the product lipid was monitored with phosphomolybdate reagent and iodine vapor. Any unreacted $DC_{8,9}PC$ was removed by chromatography on a silica column using the following gradient: 2 col. volumes $CHCl_3$; 2 col. volumes 19/1 $CHCl_3/MeOH$; 3 col. volumes 9/1 $CHCl_3/MeOH$. To insure the absence of any ion, the lipids were dissolved in $CHCl_3$ and treated with an ion exchange resin (Biorad AG 50W-X8). The lipid was then dissolved in a minimum amount of warm $CHCl_3$ and precipitated at 0° C. with acetone.

Some Examples illustrative of the invention will now be given.

EXAMPLE 1

Synthesis of Phosphatidyldiethyleneglycol

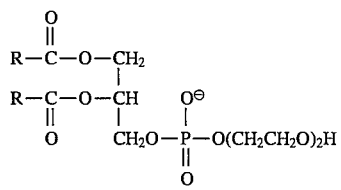

500 mg (0.55 mmol) of $DC_{8,9}PC$ was reacted with 5.8 g (55 mmol) of diethylene glycol in 50 mL of dry ether and 47 mL enzyme-buffer solution (made by mixing 30 mL of phospholipase D extract and 17 mL of acetate buffer) according to the above-discussed general procedure. The contents were stirred at 37° C. in the dark. After workup and chromatography according to the general procedure, phosphatidyldiethyleneglycol was collected in 25% yield. $^1H$ NMR ($CDCl_3$) $\delta 0.88$ (t, 6H, —$CH_3$), 1.26 (sharp singlet merged with multiplet, 44H) and 1.46–1.53 (m, 12H for —($CH_2$)—), 2.22–2.29 (m, 12H, —C≡C—$CH_2$— and O—C(O)C$_2$—), 3.65–3.81 (m, 8H, —$CH_2$—O—, —$CH_2$—OH), 4.03 (m center, 4H, —$CH_2$—O—P—O—$CH_2$—) and 5.25 (m, 1H, —CH—O—).

EXAMPLE 2

Synthesis of $DC_{8,9}$Phosphatidylhydroxyethanol

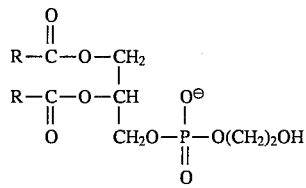

Following the general procedure, 400 mg (0.44 mmol) of $DC_{8,9}PC$ was reacted with 2.83 g (45mmol) ethylene glycol and 50 mL of dry ether in the presence of 47 mL enzyme-buffer solution (made by mixing 30 ml of phospholipase D extract and 17 mL of acetate buffer). The contents were stirred at 37° C. After the workup of the general procedure, 390 mg crude lipid was obtained which after purification afforded 300 mg (yield 77%) of pure product. TLC analysis using solvent A revealed the homogeneity of the compound ($R_f$=0.53). $^1H$ NMR (300 MHz, $CDCl_3$) $\delta 0.88$ (t, 6H, —$CH_3$), 1.22–1.44 (s, 44H) merged with 1.44–1.63 (m, 12H, total 56H, —($CH_2$)), 2.21–2.35 (m, 12H, —C≡C—$CH_2$— and O—C(O)$CH_2$—), 3.75 (s, 2H, —$CH_2$—OH), 3.99 (s, 4H, —$CH_2$—O) 4.12–4.26 (m, 1H, —H—CH—O—), 4.34 (dd, J=4.2 and 11.9 Hz, 1H, —H—CH—O—), and 5.25 (p, 1H, —CH—O—). Negative ion mass spectra produced parent ion peak at 871.3 (M–1).

EXAMPLE 3

Synthesis of $DC_{8,9}$Phosphatidylhydroxypropanol

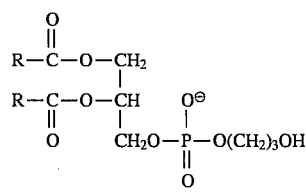

Following the general procedure, 500 mg of $DC_{8,9}PC$ in 50 mL of dry ether was reacted with 3.95 mL of 1,3 propanediol in the presence of 47 mL enzyme-buffer solution (17 mL acetate buffer added to 30 mL phospholipase D extract). Upon workup and acetone precipitation of the general procedure, a quantitative yield of $DC_{8,9}$phosphatidylhydroxypropanol was obtained. $^1H$ NMR (300 MHz, $CDCl_3$) $\delta 0.88$ (t, 6H, —$CH_3$), 1.2–1.44 (m with sharp singlet, 46H) and 1.44–1.63 (m, 12H, total 58H, —($CH_2$)—), 2.21–2.35 (m, 12H, —C≡C—$CH_2$— and O—C(O)$CH_2$—), 3.70 (s, 2—$CH_2$—OH), 4.04–4.3 (broad m, 6H, —$CH_2$—O) and 5.25 (m, 1H, —CH—O—).

EXAMPLE 4

Synthesis of $DC_{8,9}$Phosphatidylhydroxybutanol $$\begin{array}{c}
\text{O} \\
\parallel \\
\text{R}-\text{C}-\text{O}-\text{CH}_2 \\
\quad\quad\quad\quad\quad | \\
\text{R}-\text{C}-\text{O}-\text{CH} \quad\quad \text{O}^{\ominus} \\
\parallel \quad\quad\quad\quad | \quad\quad | \\
\text{O} \quad\quad \text{CH}_2\text{O}-\text{P}-\text{O}(\text{CH}_2)_4\text{OH} \\
\quad\quad\quad\quad\quad\quad \parallel \\
\quad\quad\quad\quad\quad\quad \text{O}
\end{array}$$

Following the general procedure, 500 mg of $DC_{8,9}$PC in 50 mL dry ether was reacted with 4.84 mL of 1,4-butanediol in the presence of 30 mL phospholipase D extract diluted with 17 mL acetate buffer. Workup followed by acetone precipitation of the general procedure provided a quantitative yield of $DC_{8,9}$phosphatidylhydroxybutanol. $^1$H NMR (300 MHz, CDCl$_3$) δ0.88 (t, 6H, —CH$_3$), 1.2–1.44 (m with a sharp singlet, 48H) and 1.44–1.63 (m, 12H, total 60H, —(CH$_2$)—), 2.24 and 2.33 (t center, J=6.9 Hz, 8H and J=7.1 Hz, 4H for —C≡C—CH$_2$— and O—C(O)CH$_2$— resp.), 3.71 (t, 2H, —CH$_2$—OH), 4.04–4.21 (m, 4H, —CH$_2$—O), 4.36 (d, 2H, J=11.9 Hz, 1H, —H—CH—O—) and 5.25 (m, 1H, —CH—O—).

EXAMPLE 5

Synthesis of $DC_{8,9}$Phosphatidylglycerol $$\begin{array}{c}
\text{O} \\
\parallel \\
\text{R}-\text{C}-\text{O}-\text{CH}_2 \\
\quad\quad\quad\quad\quad | \\
\text{R}-\text{C}-\text{O}-\text{CH} \quad\quad \text{O}^{\ominus} \\
\parallel \quad\quad\quad\quad | \quad\quad | \\
\text{O} \quad\quad \text{CH}_2\text{O}-\text{P}-\text{OCH}_2-\text{CHOH}-\text{CH}_2\text{OH} \\
\quad\quad\quad\quad\quad\quad \parallel \\
\quad\quad\quad\quad\quad\quad \text{O}
\end{array}$$

Following the general procedure, 538 mg (0.59 mmol) of $DC_{8,9}$PC was reacted with 5.31 g (59 mmol) glycerol dissolved in 48 mL ether in the presence of 47 mL enzyme-buffer solution. After workup and chromatography on a silica gel column following the general procedure, 290 mg (54% yield) lipid $DC_{8,9}$phosphatidylglycerol was obtained as a light yellow wax.

EXAMPLE 6

Synthesis of $DC_{8,9}$Phosphatidyl-2-chloroalkanols $$\begin{array}{c}
\text{O} \\
\parallel \\
\text{R}-\text{C}-\text{O}-\text{CH}_2 \\
\quad\quad\quad\quad\quad | \\
\text{R}-\text{C}-\text{O}-\text{CH} \quad\quad \text{O}^{\ominus} \\
\parallel \quad\quad\quad\quad | \quad\quad | \\
\text{O} \quad\quad \text{CH}_2\text{O}-\text{P}-\text{O}(\text{CH}_2)_n\text{Cl} \\
\quad\quad\quad\quad\quad\quad \parallel \\
\quad\quad\quad\quad\quad\quad \text{O}
\end{array}$$

Synthesis of chloroalkanols was carried out by reacting $DC_{8,9}$phosphatidylhydroxyethanol of Example 2 and $DC_{8,9}$phosphatidylhydroxybutanol of Example 4 with 1-chloro-N,N,2-trimethylpropenylamine in chloroform-d. 1-chloro-N,N,2-trimethylpropenylamine has the following formula:

$$\begin{array}{c}
\text{CH}_3 \quad\quad\quad \text{Cl} \\
\quad\backslash \quad\quad / \\
\quad\quad \text{C}=\text{C} \\
\quad / \quad\quad \backslash \\
\text{CH}_3 \quad\quad\quad \text{NMe}_2
\end{array}$$

which can be made, for example, according to the processes disclosed in Munyemana et al., *Tetrahedron Lett.*, vol.30, p. 3077, 1989 and Haveaux et al., *Org. Synth.*, vol. 59, p. 26, 1980. The course of the reaction was followed by NMR. In the case of $DC_{8,9}$phosphatidylhydroxyethanol, disappearance of chemical shift at δ3.75 (—CH$_2$—OH) and appearance at δ3.66 (—CH$_2$—Cl) was observed. In the case of $DC_{8,9}$phosphatidylhydroxybutanol, the ratio of chemical shifts due to —CH$_2$—OH (δ3.71) and —CH$_2$—Cl (δ3.59) was measured to monitor the course of the reaction. In both the cases, reaction was found to be complete in 30 minutes. TLC analysis using solvent A revealed the complete absence of $DC_{8,9}$phosphatidylhydroxyethanol or $DC_{8,9}$phosphatidylhydroxybutanol (R$_f$ of 0.53 $DC_{8,9}$phosphatidyl-2-chloroalkanols is 0.61).

EXAMPLE 7

Synthesis of $DC_{8,9}$Phosphatidyl-2-chloroethanol $$\begin{array}{c}
\text{O} \\
\parallel \\
\text{R}-\text{C}-\text{O}-\text{CH}_2 \\
\quad\quad\quad\quad\quad | \\
\text{R}-\text{C}-\text{O}-\text{CH} \quad\quad \text{O}^{\ominus} \\
\parallel \quad\quad\quad\quad | \quad\quad | \\
\text{O} \quad\quad \text{CH}_2\text{O}-\text{P}-\text{O}(\text{CH}_2)_2\text{Cl} \\
\quad\quad\quad\quad\quad\quad \parallel \\
\quad\quad\quad\quad\quad\quad \text{O}
\end{array}$$

Phospholipid $DC_{8,9}$phosphatidylhydroxyethanol of Example 2 (400 mg, 0.46 mmol) was reacted with 1-chloro-N,N,2-trimethylpropenylamine (400 mg, 3 mmol) in 4 mL of freshly distilled chloroform (distilled over P$_2$O$_5$). The reaction mixture was carried out at room temperature under nitrogen. The course of reaction was monitored by TLC using solvent A. After completion of the reaction, the excess chloroform was removed and the residue was chromatographed on a column of silica gel. Elution with chloroform-methanol (9:1) provided 374 mg $DC_{8,9}$phosphatidyl-2-chloroethanol as white wax in 91% yield. $^1$H NMR (300 MHz, CDCl$_3$) δ0.88 (t, 6H, —CH$_3$), 1.22–1.44 (s, 44H) merged with 1.44–1.63 (m, 12H, total 56H, —(CH$_2$)—), 2.21–2.35 (m, 12H, —C≡C—CH$_2$— and O—C(O)CH$_2$—), 3.66 (s, 2H, —CH$_2$—Cl), 3.99 (s, 4H, —CH$_2$O), 4.12–4.44 (m, 2H, —H—CH—O—), and 5.25 (m, 1H—O—).

EXAMPLE 8

Synthesis of $DC_{8,9}$Phosphatidyl-2-(hydroxyethyl)-maleic acid $$\begin{array}{c}
\text{O} \\
\parallel \\
\text{R}-\text{C}-\text{O}-\text{CH}_2 \\
\quad\quad\quad\quad\quad | \\
\text{R}-\text{C}-\text{O}-\text{CH} \quad\quad \text{O}^{\ominus} \quad\quad\quad\quad \text{H} \\
\parallel \quad\quad\quad\quad | \quad\quad | \quad\quad\quad\quad\quad \backslash \\
\text{O} \quad\quad \text{CH}_2\text{O}-\text{P}-\text{O}(\text{CH}_2)_n\text{O} \quad\quad \text{C} \quad\quad\quad \text{COOH} \\
\quad\quad\quad\quad\quad\quad \parallel \quad\quad\quad\quad\quad \backslash \quad / \\
\quad\quad\quad\quad\quad\quad \text{O} \quad\quad\quad\quad\quad\quad \text{C} \quad\quad \text{C} \\
\quad\quad\quad\quad\quad\quad\quad\quad\quad\quad\quad\quad\quad \parallel \\
\quad\quad\quad\quad\quad\quad\quad\quad\quad\quad\quad\quad\quad \text{O} \quad\quad \text{H}
\end{array}$$

49.0 mg of $DC_{8,9}$phosphatidylhydroxyethanol of Example 2 (0.056 mmol) was reacted with 40 mg (0.4 mmol) maleic anhydride in 1 mL pyridine. Maleic anhydride has the formula

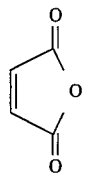

After stirring at room temperature for overnight most of the $DC_{8,9}$phosphatidylhydroxyethanol was found consumed with an emerging new spot at lower $R_f$ on TLC plate (solvent A). The product was dissolved in 2:1 chloroform/methanol and the pyridine was removed by washing with 10% aq. copper sulfate. After removing all the pyridine, the lipid solution was washed with 2% hydrochloric acid and the solvent was removed. The residue was chromatographed on a column of silica gel to afford 23 mg of $DC_{8,9}$phosphatidyl-2-(hydroxyethyl)-maleic acid (42% yield). $^1$H NMR (300 MHz, $CDCl_3$) δ0.88 (t, 6H, —$CH_3$), 1.22–1.44 (s, 44H) merged with 1.44–1.63 (m, 12H, total 56H, —($CH_2$)—), 2.21–2.35 (m, 14H, —C≡C—$CH_2$— and O—C(O)$CH_2$—), 4.02–4.45 (m, 6H, —$CH_2$—O—), 5.25 (m, 1H, —CH—O—), 6.28 (d, J=12.6 Hz, 1H, —CH=C—), and 6.4 (d, J=12.6 Hz, 1H, —C=CH—).

EXAMPLE 9

Synthesis of $DC_{8,9}$Phosphatidyl-N-methylaminoethanol,

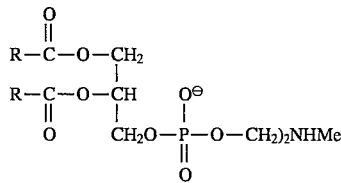

In a teflon capped reaction tube, 30 mg (0.034 mmol) of $DC_{8,9}$phosphatidyl-2-chloroethanol from Example 7 dissolved in methylene chloride was reacted with excess of dry methylamine ($NH_2Me$) dissolved in methylene chloride. The contents were stirred at room temperature in a tightly closed reaction tube. TLC analysis using solvent system A revealed the disappearance of $DC_{8,9}$phosphatidyl-2-chloroethanol and emergence of a new spot at $R_f$ 0.40 within three hours due to $DC_{8,9}$phosphatidyl-N-methylaminoethanol. After 4 hours of standing at room temperature TLC analysis revealed the appearance of a slow moving spot. The reaction was stopped by removing solvent and methylamine by rotary evaporation. The mixture was separated on a column of silica gel (elution with chloroform-methanol, 9:1). During workup and chromatography steps some hydrolysis was observed. Due to this reason variable yields were obtained with the minimum yield being 30%. The slow moving spot was identified as the lyso analogue by NMR. $^1$H NMR (300 MHz, $CDCl_3$) δ0.88 (t, 6H, —$CH_3$), 1.22–1.44 (s, 44H) merged with 1.44–1.63 (m, 12H, total 56H, —($CH_2$)—), 2.21–2.35 (m, 12H, —C≡C—$CH_2$— and O—C(O)$CH_2$—), 3.01 (s, 3H, $CH_3$—N), 3.43 (s, 2H, —$CH_2$—N), 3.99 (s, 4H, —$CH_2$—O), 4.12–4.40 (m, 2H, —H—CH—O—), and 5.25 (p, 1H, —CH—O—).

EXAMPLE 10

Synthesis of $DC_{8,9}$Phosphatidyl-N,N-dimethylaminoethanol

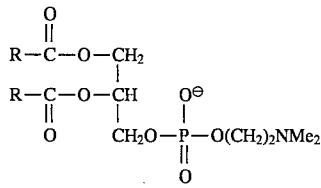

In a teflon capped reaction tube, 30 mg (0.034 mmol) of $DC_{8,9}$phosphatidyl-2-chloroethanol dissolved in methylene chloride was reacted with an excess of dry dimethylamine ($HNMe_2$) dissolved in methylene chloride. The reaction mixture was tightly closed in a reaction tube and stirred at room temperature. Within one hour, TLC analysis (solvent system A) revealed the disappearance of $DC_{8,9}$Phosphatidyl-2-chloroethanol and emergence of a new spot at $R_f$ 0.57 due to $DC_{8,9}$phosphatidyl-N,N-dimethylaminoethanol. After 4 hours of standing at room temperature TLC revealed the appearance of a spot moving at $R_f$ 0.25 (lyso analogue). The reaction products were separated on a column of silica gel (elution with chloroform-methanol, 9:1). $^1$H NMR (300 MHz, $CDCl_3$) δ0.88 (t, 6H, —$CH_3$), 1.22–1.44 (s, 44H) merged with 1.44–1.63 (m, 12H, total 56H, —($CH_2$)—), 2.21–2.35 (m, 12H, —C≡C—$CH_2$— and O—C(O)$CH_2$—), 2.94 (s, 3H, —CH—N), 3.01 (s, 3H, $CH_3$—N), 3.43 (s, 2H, —$CH_2$—N), 3.99 (s, 4H, —$CH_2$—O), 4.12–4.40 (m, 2H, —H—CH—O—), and 5.25 (p, 1H, —CH—O—). Negative ion mass spectrum revealed parent ion peak at 898.5 (M–1).

EXAMPLE 11

Synthesis of $DC_{8,9}$Phosphatidylethanol-2-chlorosulfonate

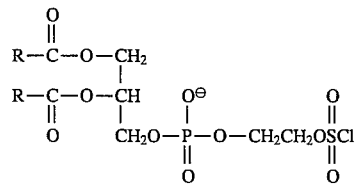

$DC_{8,9}$phosphatidylhydroxyethanol from Example 2 (169 mg, 0.19 mmol) was reacted with a ten-fold excess of sulfuryl chloride ($SO_2Cl_2$) in chloroform at room temperature. The HCl generated during the reaction mixture was removed by a gentle stream of dry nitrogen bubbled through the solution. The completion of the reaction was confirmed by TLC. TLC plates developed with chloroform:methanol:water (65:25:4) revealed an $R_f$ of 0.67, which was higher than that of $DC_{8,9}$phosphatidylhydroxyethanol (0.50). The reaction was found complete in two hours. The solvent and the excess sulfuryl chloride was removed under vacuum to give $DC_{8,9}$phosphatidylethanol-2-chlorosulfonate NMR ($CDCl_3$) δ$_{ppm}$ 0.88 (t, 6H, $CH_3$), 1.25 (m with emerging s, 44H, —($CH_2$)—), 1.71 (m center, 12H, —$CH_2$—$CH_2$—COO, and —$CH_2$—$CH_2$—C≡C—), 2.24–2.50 (m center, 12H, —$CH_2$—COO, and —$CH_2$—C≡C—), 4.41–4.51 (m, 8H, —$OCH_2$), and 5.18–5.33 (m center, 1H, —CHO—).

EXAMPLE 12

Step A: Synthesis of N,N (bis carboxymethyl) ethanolamine.

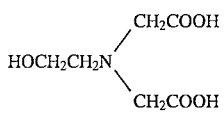

Reaction between 2.66 g (20 mmol) of iminodiacetic acid (IDA) dissolved in 9 mL, 7N aqueous KOH, and bromoethanol (6.2 g, 49 mmol) was carried out by stirring the mixture at 20° C. for 72 hours. The reaction was monitored by TLC employing methanol:10% ammonium acetate (2:1) as the solvent system. Starting material IDA showed lower $R_f$ (0.28) than that of N,N (bis carboxymethyl) ethanolamine (0.4). After removal of the solvent, the resulting residue was washed with methanol. The methanol solution contained N,N (bis carboxymethyl) ethanolamine and unreacted bromoethanol. N,N (bis carboxymethyl) ethanolamine was separated from the reaction mixture first by column chromatography using a methanol:ammonium acetate solvent system. The chromatographed product contained ammonium acetate as a contaminant, which was removed by dissolving the compound in methanol and crystallizing out the salt. Removal of the solvent gave 0.8 g (23% yield) of pure N,N (bis carboxymethyl) ethanolamine. NMR ($D_2O$) $\delta_{ppm}$ 3.2 (t center, 2H, HO—$CH_2$—$CH_2$—N), 3.66 (s, 4H, —$CH_2$—N—($CH_2$)$_2$), and 3.71 (t center, 2H, HO—$CH_2$—$CH_2$—N). IR 1640 ($COO^-$) cm$^{-1}$.

Step B: Synthesis of 1,2-bis(tricosa- 10,12-diynoyl)-sn-glycero-3-phospho-(ethanol,N,N bis carboxymethyl,N ethyl) sulfonate.

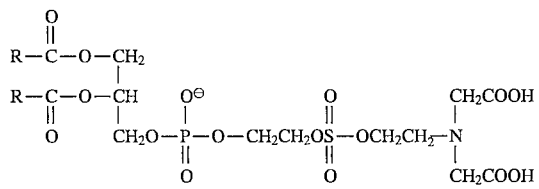

The chloroform solution of $DC_{8,9}$phosphatidylethanol-2-chlorosulfonate from Example 11 was reacted with N,N (bis carboxymethyl) ethanolamine from Step A. $DC_{8,9}$phosphatidylethanol- 2-chlorosulfonate was used in this step as such without further purification. The reaction mixture was stirred at room temperature for 24 hours under nitrogen atmosphere. At this time the reaction seemed complete, as indicated by TLC analysis of two chromatograms taken at an interval of 2 hours. Chromatography of the crude reaction product on a silica column, developed with chloroform:methanol:water (65:25:4), afforded 69 mg (36%) of 1,2-bis(tricosa-10,12-diynoyl)-sn-glycero-3-phospho-(ethanol, N,N bis carboxymethyl,N ethyl) sulfonate, which was revealed as a single spot on TLC in the same solvent system as used for column chromatography ($R_f$-0.59). NMR ($CDCl_3$) $\delta_{ppm}$ 0.88 (t, 6H, $CH_3$), 1.25 (br s, 44H, —($CH_2$)—), 1.71 (m center, 12H, —$CH_2$—$CH_2$—COO, and —$CH_2$—$CH_2$—C≡C—), 2.24–2.50 (m center, 12H, —$CH_2$—COO, and —$CH_2$—C≡C—), 3.7 (m center, 4H, —N—($CH_2$—COOH)$_2$), 3.9–4.6 (m, 8H, —$OCH_2$), and 5.15–5.41 (m center, 1H, —CHO—). IR (film) 2217 (vw,br), 1460 (S=O), 1244 (PO), 1337 (SO) cm$^{-1}$.

Numerous modifications and adaptations of the present invention will be apparent to those skilled in the art. For example, with respect to Examples 9 and 10, another amino containing compound, such as iminodiacetic acid, may be used instead of methylamine and dimethylamine, respectively. Thus, it is intended by the following claims to cover all modifications and adaptations which fall within the true spirit and scope of the invention.

What is claimed is:

1. A method for the preparation of phospholipids having modified headgroups, said method comprising the steps of:
   a) preparing a first mixture of a diacetylenic phospholipid, a crude extract of phospholipase D from white leaves of cabbage, and an alcohol containing at least two primary hydroxyl groups per molecule;
   b) reacting said first mixture, in the presence of calcium ions, so as to form, by a phospholipase D enzyme-mediated reaction a reacted mixture including a phosphatidylhydroxyalkanol, said calcium ions being present at a concentration effective to promote said phospholipase D enzyme-mediated formation of said phosphatidylhydroxyalkanol from said diacetylenic phospholipid;
   c) extracting said phosphatidylhydroxyalkanol from said reacted mixture;
   d) preparing a third mixture of said phosphatidylhydroxyalkanol and maleic anhydride;
   e) reacting said third mixture so as to form a phosphatidyl 2-(hydroxyalkyl)-maleic acid; and
   f) extracting said phosphatidyl 2-(hydroxyalkyl)-maleic acid from said third mixture.

2. A method for the preparation of phospholipids having modified headgroups, said method comprising the steps of:
   a) preparing a first mixture of 1,2-bis(tricosa- 10,12-diynoyl)-sn-glycero-3-phosphocholine, a crude extract of phospholipase D from white leaves of cabbage, and ethylene glycol;
   b) reacting said first mixture, in the presence of calcium ions, so as to form, by a phospholipase D enzyme-mediated reaction a reacted mixture including phosphatidylhydroxyethanol, said calcium ions being present at a concentration effective to promote said phospholipase D enzyme-mediated formation of said phosphatidylhydroxyalkanol from said 1,2-bis(tricosa-10,12-diynoyl)-sn-glycero-3-phosphocholine;
   c) extracting said phosphatidylhydroxyethanol from said reacted mixture;
   d) preparing a third mixture of said phosphatidylhydroxyethanol and maleic anhydride;
   e) reacting said third mixture so as to form phosphatidyl 2-(hydroxyethyl)-maleic acid; and
   f) extracting said phosphatidyl 2-(hydroxyethyl)-maleic acid from said third mixture.

* * * * *